United States Patent [19]

Otter et al.

[11] 4,031,040

[45] June 21, 1977

[54] POLYURETHANES PREPARED FROM HYDROXYMETHYL ISOCYANURATES

[75] Inventors: Marinus J.A.M. Den Otter, Munstergeleen; Anne Te Nijenhuis; Albert A. Van Geenen, both of Brunssum, all of Netherlands

[73] Assignee: Stamicarbon B.V., Geleen, Netherlands

[22] Filed: June 20, 1975

[21] Appl. No.: 588,944

[30] Foreign Application Priority Data

June 20, 1974 Netherlands ............... 7408244
June 12, 1975 Netherlands ............... 7506981

[52] U.S. Cl. ............. 260/2.5 AW; 260/2.5 AM; 260/2.5 AP; 260/2.5 AQ; 260/77.5 AM; 260/77.5 AP; 260/77.5 AQ; 260/77.5 NC

[51] Int. Cl.$^2$ ......................................... C08G 18/14

[58] Field of Search ............. 260/2.5 AQ, 2.5 AM, 260/2.5 AW, 77.5 NC, 77.5 AP, 77.5 AQ, 77.5 AM, 2.5 AP

[56] References Cited

UNITED STATES PATENTS

| | | | |
|---|---|---|---|
| 3,121,082 | 2/1964 | Guttag | 260/2.5 AW |
| 3,174,950 | 3/1965 | Cordier | 260/77.5 NC |
| 3,342,780 | 9/1967 | Meyer et al. | 260/77.5 NC |
| 3,448,084 | 6/1969 | Burdick et al. | 260/77.5 NC |
| 3,462,381 | 8/1969 | Eaton et al. | 260/77.5 AQ |
| 3,480,589 | 11/1969 | Jordan | 260/77.5 NC |
| 3,719,615 | 6/1973 | Buisson et al. | 260/2.5 AW |
| 3,730,923 | 5/1973 | Formaini et al. | 260/2.5 AW |
| 3,737,432 | 6/1973 | George et al. | 260/77.5 NC |
| 3,748,315 | 7/1973 | Wooster et al. | 260/77.5 NC |
| 3,856,718 | 12/1974 | Taub | 260/77.5 NC |

*Primary Examiner*—Eugene C. Rzucidlo
*Attorney, Agent, or Firm*—Cushman, Darby & Cushman

[57] ABSTRACT

New polyurethanes containing free isocyanurate rings are produced by mixing a hydroxymethyl isocyanurate or a derivative thereof with a polyisocyanate or a mixture of polyisocyanates.

19 Claims, No Drawings

POLYURETHANES PREPARED FROM HYDROXYMETHYL ISOCYANURATES

BACKGROUND OF THE INVENTION

The invention relates to polyurethanes containing isocyanurate rings, and in particular to polyurethane foams containing isocyanurate rings, which are also referred to as polyisocyanurate foam. The invention also relates to the process of preparing polyisocyanurate foams.

Polyurethanes that contain isocyanurate rings incorporated into the polymer are generally prepared by reacting a polyisocyanate with a polyol under conditions that promote the trimerization of the polyisocyanate to form an isocyanuric-acid derivative.

A drawback of that method of preparation is that a considerable quantity of the expensive polyisocyanate entering the reaction is consumed in the formation of the isocyanurate rings.

This drawback can be obviated by employing as a reactant a polyol containing an isocyanurate ring, for instance, tris-beta-hydroxyethyl isocyanurate. However, this compound has a melting point of over 100° C and, hence, is difficult to process. The reaction product of isocyanuric acid, formaldehyde and an amino alcohol containing a primary or secondary amino group has been proposed as an alternative reactant. The aforementioned reaction product is characterized by the inherent drawback that the amino groups incorporated into the polyol act as a catalyst for the reactions with isocyanates, so that choice of catalyst with respect to amount and type, as best suited to the processing conditions, is severely curtailed.

The object of the invention is the production of polyurethanes containing isocyanurate rings from cheap starting materials, in which the isocyanurate rings are not obtained by trimerization of polyisocyanates. In particular, the object is the preparation of polyurethane foam containing isocyanurate rings.

SUMMARY OF THE INVENTION

According to the invention, polyurethanes containing isocyanurate rings can be prepared by reaction of:

a. a polyol from the group consisting of tris-hydroxymethyl isocyanurate, bis-hydroxymethyl isocyanurate, mixed hydroxymethyl-hydroxy ($C_2$ – $C_6$ alkyl) isocyanurates, derivatives of bis- or tris-hydroxymethyl isocyanurate or a mixed hydroxymethyl-hydroxy ($C_2$ – $C_6$ alkyl) isocyanurate in which one or more hydroxymethyl groups have been replaced by hydroxylpolyoxymethylene groups containing 2–4 oxymethylene groups, oligomers obtained by condensation of the above-mentioned compounds, derivatives of said compounds in which the hydroxy groups are partly etherified and/or esterified, and mixtures of these compounds, is made to react with a polyisocyanate or a mixture of polyisocyanates in the presence of one or more compounds accelerating the reaction of isocyanate groups with hydroxyl groups b. a polyisocyanate or a mixture of polyisocyanates; and c. one or more compounds that accelerate the reaction of isocyanate groups with hydroxyl groups, optionally in the presence of (1) a solvent or mixture of solvents, (2) one or more compounds generating a gas under the reaction conditions, (3) pigments, (4) fillers, (5) reinforcing agents, (6) surface-active agents, (7) fireproofing agents, etc.

The polyurethanes obtained in this way are self-extinguishing and have a high resistance to higher temperatures. The latter characteristic is remarkable in view of the fact that hydroxymethyl isocyanurates themselves start decomposing at a temperature over about 75° C. A special advantage is that tris-hydroxymethyl isocyanurate can be prepared in a simple way from inexpensive starting materials.

A particular aim of the invention is the preparation of polyurethane foams by carrying out the reaction in the presence of blowing agents: self-extinguishing, hard or semi-hard foams are obtained which may be used as insulation material. The application of this material is mainly in insulating houses, commercial buildings, and means of transport. The foam obtained by the process according to the invention has a regular structure with mainly small closed cells. The foam may be used as such or may be processed into sandwich structural materials.

DETAILED DESCRIPTION OF THE INVENTION

According to the invention, polyurethanes containing isocyanurate rings can be prepared by reaction of:

a. a polyol from the group consisting of tris-hydroxymethyl isocyanurate, bis-hydroxymethyl isocyanurate, mixed hydroxymethyl-hydroxy ($C_2$ – $C_6$ alkyl) isocyanurates, derivatives of bis- or tris-hydroxymethyl isocyanurate or a mixed hydroxymethyl-hydroxy ($C_2$ – $C_6$ alkyl) isocyanurate in which one or more hydroxymethyl groups have been replaced by hydroxypolyoxymethylene groups containing 2–4 oxymethylene groups, oligomers obtained by condensation of the above-mentioned compounds, derivatives of said compounds in which the hydroxy groups are partly etherified and/or esterified, and mixtures of these compounds, with b. a polyisocyanate or a mixture of polyisocyanates, and c. one or more compounds that accelerate the reactions of isocyanate groups with hydroxyl groups, if so desired in the presence of a solvent or mixture of solvents, one or more compounds generating a gas under the reaction conditions, pigments, fillers, reinforcing agents, surface-active agents, fire-extinguishing compounds, etc.

The polyurethanes obtained in this way are self-extinguishing and have a high resistance to higher temperatures. The latter is remarkable because hydroxymethyl isocyanurate themselves start decomposing at a temperature over about 75° C. A special advantage is that tris-hydroxymethyl isocyanurate can be prepared in a very simple way from inexpensive starting materials.

A particular aim of the invention is the preparation of foamy polyurethanes by carrying out the reaction in the presence of blowing agents. In this way self-extinguishing, hard or semi-hard foams are obtained which may be used, i.a., as insulation material. The application of this material is mainly in the domain of houses, utility buildings, and means of transport. By means of the process according to the invention both foams with closed cells and foams with open cells can be obtained. The foam may be used as such or may be worked up in sandwich structures.

Wherever this-hydroxymethyl isocyanurate is mentioned in the text, the term is used, unless specifically stated otherwise, to include the mixtures of tris-hydroxymethyl isocyanurate with bis-hydroxymethyl isocyanurate and/or with generally minor amounts of these compounds in which one or more hydroxymethyl groups have been replaced by hydroxypoly-oxymethylene groups containing 2–4 oxymethylene units, and/or with oligomers obtained by condensation of the above compounds. These mixtures generally consist of at least 50 moles %, and mostly at least 70 moles %, of tris-hydroxymethyl isocyanurate itself, and generally of 0–30 moles %, mostly 0–25 moles %, of bis-hydroxymethyl isocyanurate.

Bis-hydroxymethyl isocyanurate can be prepared by separating off formaldehyde from tris-hydroxymethyl isocyanurate by means of careful heat-treatment, for instance at 75°–80° C. Also the bis-hydroxymethyl isocyanurate generally contains subordinate quantities of oligomers and the like.

Mixed hydroxymethyl-hydroxy ($C_2 - C_6$ alkyl) isocyanurates can be prepared by having tris-hydroxymethyl cyanurate react with an oxirane with 2–6 carbon atoms, causing one or two of the hydroxymethyl groups to be replaced by a higher hydroxyalkyl group. Examples of suitable oxiranes are ethylene oxide, propylene oxide, 2,3-epoxybutane and 1,2-epoxyhexane. Application of propylene oxide or higher 1,2-epoxy compounds will result in the formation of polyols with one, resp. two, primary hydroxyl groups (the hydroxymethyl groups) and two, resp. one, secondary hydroxyl groups, so that a polyol with hydroxyl groups of different reactivities forms, which involves advantages.

In some cases it is advantageous for part of the hydroxy groups of the hydroxyalkyl isocyanurate, for instance at most one third part, to be etherified or esterified. To this end the hydroxyalkyl isocyanurate is reacted with a deficient amount of acylating or etherifying agent, for instance an acid, acid anhydride, acid chloride or alcohol, like an aliphatic or aromatic carboxylic acid with 1–7 carbon atoms or the anhydride or acid chloride thereof or an aliphatic alcohol with 1–6 carbon atoms. For reaction conditions possibly to be applied in this kind of etherifications and esterifications reference is made to Ukrainan Chemical Journal 30, No. 2, pages 195–198 (1964), the disclosure of which is incorporated herein by reference.

The tris-hydroxymethyl isocyanurate to be used according to the invention can be prepared by making cyanuric acid react with formaldehyde of with a compound splitting off formaldehyde, such as paraformaldehyde. The reaction can be effected, for instance, in water or in a substantially inert, aprotic polar solvent or mixture of solvents.

Some suitable solvents are nitriles and ketones, such as acetonitrile, cyclohexanone, methyl-ethyl ketone, or, e.g. dimethyl formamide, dioxane, pyridine, or liquid, fire-extinguishing compounds, like tris(2-chlorethyl)phosphate. The reaction of cyanuric acid with paraformaldehyde in an organic solvent generally proceeds more smoothly if a small catalytic amount of acid or base is present.

The reaction may be carried out at a temperature up to 100° C, preferably at 50° to 90° C. The pressure is of little importance: both normal pressure and elevated pressures are possible.

The ratio of the reactants may vary between a molar formaldehyde/cyanuric acid ratio of 1.5/1 and 10/1. By preference, a ratio between 2/1 and 5/1 is chosen.

The pH seems to have little influence during the reaction, and may vary between values of 1 and 7 in water. By preference, the pH is controlled to a final value of between 1 and 5.

Upon completion of the reaction, the solvent can be removed, e.g. by evaporation at reduced pressure. During the evaporation preferably a temperature of below 60° C, most preferably of about 40° C, is maintained. Tris-hydroxymethyl isocyanurate in a pure form is a compound that is solid at room temperature and is difficult to mix with the other reactants forming polyurethane. Polyols containing one or more isocyanurate rings, which polyols contain 2 or more % by weight of solvent are much easier to handle. Consequently, polyol containing one or more isocyanurate rings, which polyol contains at least 2% by weight of solvent is preferably used in the process according to the invention. It is to be recommended in this connection to choose a solvent that is volatile under the selected reaction conditions, or, just as water, reacts with one of the components to form volatile compounds. If the preparation is effected in water, the water can be replaced by an inert organic solvent by means of azeotropic distillation.

Another mode of preparation is in allowing cyanuric acid, whilst being heated, to react with paraformaldehyde in water or with a concentrated (for instance about 60% by weight) aqueous formaldehyde solution, in adding a high-boiling solvent to the solution formed and in subsequently removing practically all of the water by evaporation. In this way one can obtain, for instance, a solution, with a water content of 2% by weight, of tris-hydroxymethyl isocyanurate in the tris(2-chlorethyl) phosphate acting as solvent.

If water is used as the only solvent, polyol containing one or more isocyanurate rings, which polyol contains 3–8% by weight of water, is preferably used in the process according to the invention.

Very good results are obtained if use is made of polyol containing one or more isocyanurate rings, which polyol contains dimethyl formamide as solvent, preferably in an amount of 10–30% by weight. The fact that dimethyl formamide is not fully inert with respect to polyisocyanates appears to have no annoying consequences. If use is made of tris-hydroxymethyl isocyanurate containing dimethylformamide and of a physical blowing agent, it is possible to obtain micro-cellular, slightly resilient foams that are hard or semi-hard in dependence on the nature and the amount of catalyst and the amount of dimethyl formamide. The presence of a solvent also facilitates the mixing of the various components.

Also other polyols may be used in combination with the polyol containing one or more isocyanurate rings. For instance, as modifying and flow-improving compound an organic polyol, like an alkylene glycol with 2–12 carbon atoms or a polyoxyalkylene glycol, may be applied by the side of the polyol containing one or more isocyanurate rings. In this way a tenacious, semi-hard foam can be obtained which is less combustible than is conventional polyurethane foam.

The poly-isocyanate may be chosen from the well-known aromatic and aliphatic poly-isocyanates, such as toluene di-isocyanates, 4.4'-diphenyl methane-di-isocyanate, xylylene di-isocyanate, polymethylene-polyphenylene isocyanate, 1.6-hexamethylene di-isocyanate, tetramethylene di-isocyanate, dimethyl-cyclohexane ω.ω.'-di-isocyanate, and isophorone di-isocyanate. In general, such a ratio of the polyol to the poly-isocyanate is chosen that 1.0 to 1.5, and preferably 1.05 to 1.1, isocyanate groups per hydroxyl group are contained in the reaction mixture. If water is present in the reaction mixture, it is necessary to add an additional amount of poly-isocyanate corresponding to at least 2 isocyanate groups per molecule of water.

The catalyst may be any of the catalysts normally used in polyurethane chemistry, such as tin salts and tin complexes and compounds with a tertiary nitrogen atom. Some examples are triethylene diamine, triethyl amine, N-ethyl morpholine, N-methyl-N-dimethyl-amino-ethyl piperazine, tin octoate, dibutyl-tin dilaurate, tetrabutyl-1.3-diacetoxydistannoxane, dibutyl-tin diacetate, and dibutyl-tin oxide. The amount of catalyst may vary between 0.01 and 5 % by weight, calculated to the mixture of reactants. Use is generally made of 0.05 to 3 % by weight. The type and amount of catalyst are so chosen that, under the selected reaction conditions, sufficient time is available for complete mixing of the reactants and that the maximum evolution of gas takes place while the reaction mixture is gelated. In general, this can best be achieved by using tin compounds as the catalyst.

Foamy polyurethanes are obtained by the process according to the invention by carrying out the reaction in the presence of one or more blowing agents. The blowing agent may act chemically by decomposition or, as is the case when water is used, by reacting with the polyisocyanate with simultaneous release of a gas. Use may also be made of the usual physical blowing agents, such as low-boiling halogenated alkanes, e.g. trichlorofluoromethane, trifluorochlormethane, methylene chloride, chloroform, dichlorofluoromethane, difluorochloromethane, or dichloro-ethane. If so desired, air or an inert gas may also be blown into the reaction mixture.

To promote the mixing of the various components and to regulate the properties of the foam, one or more surface-active compounds may also be incorporated in the reaction mixture. Use may be made of surface-active compounds of the types that are well known in polyurethane chemistry, such as, e.g., terminated polyoxy-alkylenes, polyoxy-alkylated vegetable oils and fatty acids or silicone copolymers.

The reaction is carried out by mixing the tris-hydroxymethyl isocyanurate with the poly-isocyanate, the catalyst and auxiliary substances, if any. To facilitate the mixing, the tris-hydroxymethyl isocyanurate may be preheated to a temperature of about 30° to 50° C. The reaction proceeds rapidly owing to the presence of the catalyst. In most cases a solid mass is obtained within 5 minutes.

In the preparation of foamy polyurethane containing isocyanurate rings, attention must be paid to the boiling point of any physical blowing agents that are used. The foaming may be effected without pressure or with some back pressure.

If so desired, the hard or semi-hard foam obtained in this way may be heated at a higher pressure for some more time. In general, heating to 50° to 250° C for 1 to 10 hours is sufficient to improve the strength and the fire-extinguishing properties of the foam.

The poly-isocyanurate foams obtained according to the invention show a regular structure. In dependence on the method of preparation, the foam may have fine cells of, e.g., 70–150 μm in section, or may have larger cells of, e.g., 0.25 mm in section.

The density of the foam likewise depends on the reaction conditions and can amount to 10 to 100 kg/m³. If desired, also higher values can be reached. The foams with a density of between 10 and 40 kg/m³ are particularly suitable as insulation materials.

The foams obtained according to the invention are self-extinguishing and are resistant to temperatures of 300° C and higher for a short time without appreciable deterioration in properties.

The invention will be elucidated with reference to the following examples, but will not be restricted to the realizations described therein.

EXAMPLE I

The preparation of tris-hydroxymethyl isocyanurate

A. A suspension of 516 g of cyanuric acid in 1200 g of 30% formalin was heated to 80° C with stirring. Next, the reaction mixture was kept at this temperature for another 30 minutes, in which period all cyanuric acid dissolved. The reaction mixture was then cooled to 60° C, after which the reaction mixture was concentrated to a viscous clear liquid by evaporation at 55° C and at reduced pressure (about 15 mm Hg).

Analysis gave the following results:

| | |
|---|---|
| isocyanurate groups (determined as cyanuric aid | 58.1 % by weight |
| formaldehyde groups ($CH_2O$) | 37.1 % by weight |
| water | 4.0 % by weight |
| molar ratio | $CH_2O$/cyanuric acid = 2.75/1. |

In the analysis the methylol groups were converted into formaldehyde by pyrolysis in phosphoric acid and determined as such. The water content was determined by Fisher titration. Cyanuric acid was determined by diluting tris-hydroxymethyl isocyanurate with excess water and precipitating the cyanuric acid by addition of melamine.

B. 850 g of tris-hydroxymethyl isocyanurate with a water content of 0.7 % by weight were prepared in the way described under A. Then 250 ml of acetone were added to it. The mixture was subjected to an azeotropic distillation at 55° C while the pressure was gradually reduced to a final value of 15 mm Hg. This process was repeated six more times. A clear viscous liquid was finally obtained. Analysis gave the following results:

| | |
|---|---|
| cyanuric acid | 53.6 % by weight |
| formaldehyde | 35.0 |
| water | 1.4 |
| acetone | 9.0 |
| molar ratio | $CH_2O$/cyanuric acid = 2.81/1 |

C. A suspension of 23.6 g of paraform (96%) and 32.5 g of cyanuric acid in 55 ml of water-free dioxane was heated to 80° C. 1 ml of acetic acid was added and the reaction mixture was heated at 80° C for another 45 minutes, and then cooled to 60° C. Evaporation at 55° C and reduced pressure gave a clear viscous liquid. Analysis gave the following results:

| | |
|---|---|
| cyanuric acid | 46.7 % by weight |
| formaldehyde | 30.6 |
| acetic acid | 0.6 |
| dioxane | not determined |
| molar ratio | $CH_2O$/cyanuric acid = 2.82/1 |

D. A suspension of 516 g of cyanuric acid and 375 g of paraform (96%) in 800 ml of dry N.N-dimethyl formamide was heated to 80° C, after which 3 ml of tri-ethyl amine were added. After reaction for 90 minutes at 80° C the reaction mixture was cooled and evaporated at reduced pressure (about 1 mm Hg). A clear viscous liquid was obtained. Analysis gave the following results:

| cyanuric acid | 44.9 % by weight |
| formaldehyde | 28.2 |
| water | 0.06 |
| dimethyl formamide | 25.0 |
| molar ratio | $CH_2O$/cyanuric acid = 2.70/1 |

PREPARATION OF POLYURETHANE

A poly-isocyanurate foam was prepared by mixing 100 g of the tris-hydroxymethyl isocyanurate obtained in example I.A with 18 g of dimethyl formamide, 5 g of a surface-active compound (DC 193 silicone copolymer of Dow Corning), 230 g of polymethylene-polyphenylene-isocyanate and 1 ml of dibutyl-tin diacetate in a beaker by means of a high-speed stirrer. The mixture was poured into a flat box. After 15 minutes the mixture had hardened with foam formation. The hard microcellular foam obtained in this way was not brittle, but slightly resilient, and could be cut well. The density was 15 kg/m³ and the heat conductivity 0,04 kcal/m/h/° C. The oxygen index according to ASTM-D 2863-70 was 22 to 23, and, upon a thermal after-treatment (8 hours at 150° C), the oxygen index according to ASTM-D 2863-70 was 24.5.

EXAMPLE II

A polyisocyanurate foam was prepared from 100 g of the tris-hydroxymethyl isocyanurate obtained in example I.D, 10 g of L 5340 emulsifier, 130 g of polymethylene-polyphenylene-isocyanate, 25 g of methylene chloride, and 0.4 ml of dibutyl-tin diacetate in the way described in example I. The hard, slightly resilient microcellular foam obtained in this way had a density of 24 kg/m³, a coefficient of heat conduction of 0,04 kcal/m/h/° C, and after a thermal treatment of 8 hours at 150° C, an oxygen index of 24.

EXAMPLE III

Preparation of mixed hydroxymethyl-2-hydroxypropyl isocyanurate

In a flask provided with a stirrer, a heating jacket and a reflux cooler, 828 g of a 74 % by weight solution of tris-hydroxymethyl isocyanurate (molar ratio $CH_2O$/cyanuric acid = 2.87/1) in dimethylformamide with 0.2 % by weight of water were mixed with 168 g of propylene oxide and 3.6 g of triethyl amine. Next, the reaction mixture was boiled for 24 hours, with stirring and reflux. During the entire reaction the temperature did not exceed 75° C. The temperature of the reflux cooler was maintained at −25° C. By the end of the reaction, reflux had practically ceased to occur. In this way 995 g were obtained of a mixture which had a lower viscosity (224.9 cSt at 68° C) than the starting mixture. Analysis gave the following results:

| hydroxymethyl isocyanurate | 11.6 % by w. (as cyanuric acid) |
| dito, plus mixed hydroxymethyl-hydroxypropyl-isocyanurate | 35.2 % by w. (as cyanuric acid) |
| formaldehyde | 21.5 % by w. |
| water | 0.2 % by w. |
| dimethyl formamide | not determined |

Hydroxymethyl isocyanurate was determined by diluting the mixture with an excess quantity of water and by causing the cyanuric acid to precipitate through addition of melamine. The total amount of hydroxymethyl plus mixed isocyanurate was determined by titration with base.

On the basis of i.a., a nuclear spinresonance examination it was established that the mixed isocyanurate was mixed hydroxymethyl-2-hydroxypropyl isocyanurate and mainly consisted of bis-(hydroxymethyl)-mono-(2-hydroxypropyl) isocyanurate.

PREPARATION OF POLYURETHANE 100 g of the product obtained was mixed with 20 g of tris-(2-chlorethyl)phosphate, 1 g of emulsifier L 5340 (Union Carbide Corp.), 0.05 ml of dibutyl tin diacetate, 5 g of methylene chloride and 120 g of polymethylenepolyphenyl isocyanate (Desmodur 44V) in a beaker with the aid of a stirrer having a high rpm-number. The hard polyisocyanurate foam with fine cells so obtained had a density of 45 kg/m³ and a heat conductivity coefficient of 0.034 kcal/m/h/° C.

The oxygen index, determined in accordance with ASTM D 2683-70, amounted to 24.

EXAMPLE IV

A suspension of 516 g of cyanuric acid and 375 g of paraform was heated to 80° C in 300 ml of water and kept at said temperature until all solid matter had become dissolved (about 2 hours).

After having cooled in a rotating evaporator (at reduced pressure (15 mm Hg)), the solution was concentrated by evaporation as far as possible.

Thereupon, 175 g of tris-(2-chlorethyl)phosphate was added and admixed with the viscous mass. From the resulting solution some water was still removed then, again at reduced pressure. During the evaporation operations for concentration the temperature amounted to at most 57° C.

Analysis gave the following results:

| cyanuric acid | 48.4 % by w. |
| formaldehyde | 33.6 % by w. |
| tris-(2-chlorethyl)phosphate | 15.5 % by w. |
| water | 2.2 % by w. |
| molar ratio | $CH_2$/O cyanuric acid = 2.99 |

Polyisocyanurate foam was prepared by mixing 50 g of the tris-hydroxymethyl isocyanurate so obtained with 50 g of 'Desmopheen' FWFA-O (commercial product of Bayer A.G., viz. a polyol with a hydroxyl number of 325–375), 15 g of methylene chloride, 0.2 ml of dibutyl tin diacetate and 157.5 g of polymethylene-polyphenylisocyanate (Desmodur 44V) in a beaker with the aid of a stirrer having a high rpm-number.

The hard foam with fine cells obtained in this way had a density of 33 kg/m³ and a heat conductivity coefficient of 0.036 kcal/m/h/° C. The oxygen index, determined in accordance with ASTM D 2863-70, amounted to 25.

What is claimed is:

1. Process for preparing polyurethanes containing isocyanurate rings from a polyol containing one or more isocyanurate rings, this process being characterized in that said polyol selected from the group consisting of tris-hydroxymethyl isocyanurate, bis-hydroxymethyl isocyanurate, mixed hydroxymethylhydroxy ($C_2 - C_6$ alkyl) isocyanurates, derivatives of bis- or tris-hydroxymethyl isocyanurate or a mixed hydroxymethyl-hydroxy ($C_2 - C_6$ alkyl) isocyanurate in which one or more hydroxymethyl groups have been replaced by hydroxypolyoxymethylene groups containing 2–4 oxymethylene groups, oligomers obtained by intercondensation of the above-mentioned compounds during the preparation of the above-mentioned compounds, derivatives of said compounds in which the hydroxy groups are partly etherified and/or esterified, and mixtures of these compounds, is made to react with an organic polyisocyanate or a mixture of polyisocyanates, the ratio of isocyanate groups of said polyisocyanate or mixture to hydroxy groups of said polyol being between 1.0 and 1.5, in the presence of one or more compounds accelerating the reaction of isocyanate groups with hydroxyl groups, wherein said polyol contains at least 2% by weight of solvent.

2. A process for preparing a polyurethane containing isocyanurate rings, comprising reacting tris hydroxymethyl isocyanurate or a mixture thereof as hereinbefore defined, with a polyisocyanate or a mixture of polyisocyanates in the presence of one or more compounds that accelerate the reaction of isocyanate groups with hydroxyl groups.

3. A process according to claim 1, wherein the polyol containing one or more isocyanurate rings is a mixed hydroxymethyl 2-hydroxyalkyl isocyanurate.

4. A process according to claim 3, wherein the polyol containing one or more isocyanurates rings is a mixed hydroxymethyl 2-hydroxypropyl isocyanurate.

5. A process according to claim 1 which further includes at least one other different polyol.

6. A process according to claim 1 wherein the reaction is effected in the presence of one or more blowing agents, whereby a foamed polyurethane is obtained.

7. A process according to claim 1, wherein the reaction is effected in the presence of a solvent.

8. A process according to claim 7, wherein the solvent is an aliphatic or cyclo-aliphatic ketone, an aliphatic or cyclo-aliphatic nitrile, dimethyl formamide, dioxane or pyridine or a mixture containing two or more of such solvents.

9. A process according to claim 1 wherein the polyol containing one or more isocyanurate rings starting material contains from 3% to 8% by weight of water as a solvent.

10. A process according to claim 7, wherein the polyol containing one or more isocyanurate rings starting material contains from 10% to 30% by weight of dimethyl formamide as solvent.

11. A process according to claim 1, wherein the polyol containing one or more isocyanurate rings starting material is preheated to a temperature between 30° and 50° C before it is mixed with the other reactants.

12. A process according to claim 1, wherein the reaction is carried out in the presence of one or more surface-active compounds.

13. A process according to claim 1, wherein tris-hydroxymethyl isocyanurate which has been obtained by reaction of cyanuric acid with formaldehyde in the form of paraformaldehyde in a molar ratio of 1 : 2 to 1 : 5, in a substantially inert, aprotic polar organic solvent, in the presence of a catalytic amount of acid or base, is used as starting material.

14. A polyurethane or polyurethane foam, obtained by a process according to claim 1.

15. Moulded articles fully or partly formed of a polyurethane or polyurethane foam as claimed in claim 14.

16. A process according to claim 1, wherein said polyol is tris-hydroxymethyl isocyanurate.

17. A process according to claim 1, wherein said polyol is bis-hydroxymethyl isocyanurate.

18. A process according to claim 1, wherein said polyol is mixed hydroxymethyl-hydroxy ($C_2 - C_6$ alkyl) isocyanurate.

19. A process according to claim 1, wherein said polyol is provided in the form of a mixture of derivatives of bis- or tris-hydroxymethyl isocyanurate or a mixed hydroxymethylhydroxy ($C_2 - C_6$ alkyl) isocyanurate in which one or more hydroxymethyl groups have been replaced by hydroxypolyoxymethylene groups containing 2–4 oxymethylene groups.

* * * * *